US00PP09102P

United States Patent [19]

Avila

[11] Patent Number: Plant 9,102

[45] Date of Patent: Apr. 11, 1995

[54] "MADONNA SUN" PEACH TREE

[75] Inventor: Fernando C. Avila, Hanford, Calif.

[73] Assignees: Fredrick A. Avila, Walnut Creek; Jeffrey D. Avila, San Francisco, both of Calif. ; a part interest

[21] Appl. No.: 261,196

[22] Filed: Jun. 16, 1994

[51] Int. Cl.[6] ..... A01H 5/00

[52] U.S. Cl. ..... Plt./43.2

[58] Field of Search ..... Plt. 43.2

*Primary Examiner*—James R. Feyrer

*Attorney, Agent, or Firm*—Worrel & Worrel

[57] ABSTRACT

A new and distinct variety of peach tree which produces fruit ripe for commercial harvest approximately Aug. 1 to Aug. 10 in the central San Joaquin Valley of California and somewhat remotely similar to the fruit of the "O'Henry" peach tree (U.S. Plant Pat. No. 2,964), but distinguished therefrom in numerous respects including that the fruit is generally more globose in shape and of lower acidity providing a mild, pleasant flavor.

1 Drawing Sheet

BACKGROUND OF THE NEW VARIETY

The present invention relates to a new and distinct variety of peach tree, which will hereinafter be denominated varietally as the "Madonna Sun" peach tree, and, more particularly, to a peach tree which produces freestone fruit which are mature for commerical harvesting and shipment approximately Aug. 1 to Aug. 10 in the San Joaquin Valley of central California.

The development of commercial varieties of fruit trees results in a myriad of different varieties which possess a diverse combination of characteristics. Where the fruit is concerned, these characteristics may include large size, high skin coloration, pleasing shape, good flavor, or the like which may be considered commercially attractive. Other characteristics, such as the reciprocals of the foregoing, as well as poor shelf life, susceptibility to bruising, disease, or insects, or the like, may be considered to be commercially unattractive.

There are, however, some characteristics which are rarely found in any commercial varieties and particularly when present in combination with other commercially attractive attributes. One such characteristic is unusually low acidity. As a general principal, tree fruit is more flavorful where the acidity is comparatively low. Furthermore, consumers frequently have a diegestive intolerance to fruit with more normal levels of acidity. The discovery of a variety producing fruit having a lower than normal level of acidity, while otherwise possess many other commercially attractive attributes, is unusually rare. The new variety of the present invention is such a variety.

ORIGIN AND ASEXUAL REPRODUCTION OF THE NEW VARIETY

The present invention of peach tree was discovered by the inventor in about 1982 as a mutation in his orchard which is located near Hanford in the San Joaquin Valley of central California. The orchard otherwise was composed entirely of "Fayett" peach trees. The new variety was first asexually reproduced by the inventor in 1984 by grafting "Nemaguard" peach tree rootstock with scions of the new variety in the orchard of origin of the parent tree. Since such asexual reproduction, the inventor has continuously observed the asexually propagated trees and confirmed that they are in all respects identical to the parent tree.

SUMMARY OF THE NEW VARIETY

The "Madonna Sun" peach tree is characterized by producing a late season, freestone fruit of large size which has a red blush skin coloration ranging from a medium red-orange to a deep garnet red and which is ripe for commercial harvesting and shipment approximately Aug. 1 to Aug. 10 in the San Joaquin Valley of central California. The new variety can be compared with the "O'Henry" peach tree (U.S. Plant Pat. No. 2,964), which produces fruit ripening at a similar time in the growing season and which has a somewhat similar skin coloration and shape. However, the fruit of the instant variety is distinguishable from that of the 'O'-Henry" peach tree in that it possesses significantly less acidity giving it a mild, pleasant flavor; it is more globose in shape; it tends to have a somewhat more pronounced suture area; and in that it typically does not develop as dark a red blush in its skin coloration as does the fruit of the "O'Henry" peach tree.

BRIEF DESCRIPTION OF THE DRAWING

The drawing is a color photograph showing representative fruit of the peach tree of the new variety including a first in side elevation, a second showing the base end portion thereof, a third in side elevation showing the suture thereof, a fourth showing the apex end portion thereof, and a fifth sectioned and laid open to expose the pit well in one of the sections and the stone in position in the pit well in the other of the sections; and representative foliage of the new variety.

DETAILED DESCRIPTION

Referring more specifically to the pomological details of this new and distinct variety of peach tree, the following has been observed under the ecological conditions prevailing at the orchard of origin which is located near Hanford in the San Joaquin Valley of central California. All major color code designations are by reference to the *Dictionary of Color*, by Maerz and Paul, First Edition, 1930. Common color names are also occasionally employed.

TREE

Generally:

*Size.*—Produces from 3.5 feet (105 cm) to 4.5 feet (135 cm) of new growth in the top of the tree annually.

*Vigor.*—Vigorous.

*Form.*—Upright to upright-spreading and has been developed using the open vase system of training.

*Productivity.*—Productive and hardy.

*Regularity of Bearing.*—Produces crop annually under typical central San Joaquin Valley climatic conditions.

Trunk:

*Size.*—Average thickness.

*Surface texture.*—Relatively rough.

*Color.*—Dark brown-grey (8-H-11 Conga Brown).

*Lenticels.*—Numbers — Average number. Size — Medium sized lenticels present throughout the bark surface. Length — 6 mm (0.2362 inches) to 8 mm (0.3150 inches). Form — Flat oval.

Branches:

*Size.*—Average thickness.

*Surface texture.*—Relatively smooth.

*Color.*—One year or older wood — Medium brown (7-C-11 Auburn Brown). Immature branches — Pale green (20-J-3 Shadow Green). New shoots that are exposed to direct sunlight are often tinged with a rose-red hue.

*Internode.*—Length — On current season hangar wood is within normal range, from 25 mm (0.9843 inches) to 37 mm (1.457 inches) between nodes.

LEAVES

Size:

*Generally.*—Relative long and narrow. Measurement taken from large leaves near midpoint of vigorous upright current season's shoots.

*Average length.*—Range from 16.7 cm (6.575 inches) to 20.2 cm (7.953 inches).

*Average width.*—Range from 3.9 cm (1.535 inches) to 4.7 cm (1.850 inches).

Leaf Thickness: Average.

Form: Linear lanceolate. The tip form is acuminate. At times the leaves curve downwards.

Color:

*Upwardly disposed surface.*—Dark green (24-L-4).

*Downwardly disposed surface.*—Lighter grey-green (23-L-5 Cypress Green).

Marginal form:

*Generally.*—Crenate with somewhat irregular low crenations. At times the crenations are double, especially near mid-margin.

Leaf margin: Moderately undulate.

Glandular characteristics: Medium to small. From 2 to 5 reniform glands are present along the basal portion of the leaf margin. From 0 to 3 additional reniform glands can be present on the petiole or right at the petiole juncture with the basal leaf margin. The glands are usually arranged in an alternate position.

Gland:

*Color.*—Young gland is light shiny green (18-L-6 Love Bird Green), darkening and deteriorating with age.

Petiole:

*Size.*—Medium.

*Length.*—10 mm (0.3937 inches) to 13 mm (0.5118 inches).

*Thickness.*—2.0 mm (0.0787 inches) to 2.5 mm (0.0984 inches).

*Color.*—Pale green (19-K-6 Sea Green), but substantially darker green (20-K-6 Piquant Green) within the petiole groove.

Stipules:

*Size.*—Medium.

*Length.*—7 mm (0.2756 inches) to 9 mm (0.3543 inches).

*Form.*—Linear lanceolate with serrate margins.

*Color.*—Young stipules are pale green (19-L-5 Cosse Green), darkening and becoming early deciduous with age.

FLOWERS

Flower buds: Dormant floral hardy under typical San Joaquin Valley climatic conditions.

*Size.*—Medium.

*Form.*—Conic.

*Color.*—Grey (7-C-7).

*Surface texture.*—Pubescent.

Flowers:

*Generally.*—"Showy" type.

*Date of bloom.*—Average to slightly late in relation to other commercial peach varieties grown in the central San Joaquin Valley of California. Full bloom usually occurs in the first to second week of March, from Mar. 7 to Mar. 12 depending upon the winter chilling hours accumulated in any specific year.

*Size.*—Generally — medium.

*Flower — diameter.*—Ranges from 37 mm (1.457 inches) to 40 mm (1.575 inches) when the flower is fully expended.

*Bloom.*—Abundant with two floral buds usually present per node.

*Petals.*—Size — large. Length — 22 mm (0.8661 inches) to 24 mm (0.9449 inches). Width — 17 mm (0.6693 inches) to 19 mm (0.7480 inches). Form — Broadly ovate. Margins — Undulate and are often cupped inwards. Number — Five. Color — Young petals are light pink (1-C-1), becoming a darker pink (1-D-3) when fully mature. The basal area of mature petals is even darker pink (1-B-5).

*Flower pedicel.*—Size — Average, ranging from 3 mm (0.1181 inches) to 4 mm (0.1575 inches). Thickness — 1.0 mm (0.0394 inches) to 1.5 mm (0.0591 inches). Color — Light green (20-J-6).

*Nectaries.*—Color — Young nectaries is orange (11-D-11), becoming somewhat darker with age (1-C-12).

*Anthers.*—Size — Average. Color — Red (2-J-10) dorsally and buff (11-G-5) ventrally. Pollen — Abundant.

*Pollen.*—Color — Yellow (10-L-6).

*Stamens.*—Length — 12 mm (0.4724 inches) to 15 mm (0.5906 inches).

*Filament.*—Color — Light pink (1-C-1) when young, becoming darker rose-pink (1-E-5) with maturity.

*Pistil.*—Length — Average, ranging from 16 mm (0.6300 inches) to 18 mm (0.7087 inches), including the ovary. Color — Light yellow (10-F-1). Surface — Pubescent.

FRUIT

Maturity when described: Ripe for commercial harvesting and shipment usually occurs in the first week of August. In 1992, the first pick was on Aug. 1 and the last pick on Aug. 10 near Hanford of the San Joaquin Valley of central California.

Size:

*Generally.*—Large and uniform.

*Average diameter in the axial plane.*—65 mm (2.559 inches) to 68 mm (2.677 inches).

*Average diameter in the suture plane.*—73 mm (2.874 inches) to 84 mm (3.307 inches).

*Average diameter in the cheek plane.*—71 mm (2.795 inches) to 76 mm (2.992 inches).

Form:

*Uniformity.*—Usually asymmetrical with one fruit half larger than the other.

*Lateral.*—Variable, from broadly ovate to nearly oblate.

*Apical.*—Oval to nearly globose with a slightly raised ventral suture.

Suture:

*Generally.*—Distinct continuous line from base to apex, more distinct over the apical shoulder, at the apex and within the stem cavity basin. The suture often does not exhibit a distinct coloration of its own, but usually takes on the coloration of the associated ground or blush color. Slight stitching can be present on the suture.

*Ventral surface.*—Generally — Often irregular. The suture is somewhat prominent with moderate lipping, typically more prominent on one half.

Stem cavity:

*Generally.*—Moderate in size. The ventral suture line is frequently folded and occasionally clefted within the cavity basin. The fruit basal shoulders often display an indentation where the fruit was pressed next to the bearing branch.

*Width.*—Ranges from 30 mm (1.181 inches) to 37 mm (1.457 inches).

*Depth.*—Ranges from 14 mm (0.5512 inches) to 16 mm (0.6299 inches).

*Length.*—34 mm (1.339 inches) to 40 mm (1.575 inches).

*Form.*—Oval.

Stem:

*Generally.*—Average in size.

*Length.*—Ranging from 10 mm (0.3937 inches) to 12 mm (0.4724 inches).

*Thickness.*—3.0 mm (0.1181 inches) to 3.5 mm (0.1378 inches).

*Color.*—Light green (20-L-3 Certosa Green).

Base:

*Form.*—Moderately truncate.

*Angle.*—Somewhat variable, but most frequently at right angle to the fruit axis.

Apex: Variable from substantially depressed to slightly raised.

*Shape.*—A distinct depression is almost always present on both the ventral and dorsal sides of the apex.

Pistil point:

*Position.*—Oblique and recessed into the suture groove.

Skin:

*Thickness.*—Average. Skin is tenacious to the fruit flesh at commercial maturity.

*Texture.*—Surface is moderately pubescent. The pubescence is relatively short and of a light grey coloration.

*Skin flavor.*—Relatively mild and nearly neutral in acidity.

*Tendency to crack.*—No tendency to crack has been observed.

*Color — Generally.*—Relatively uneven from 80 percent to 100 percent of the fruit surface is red blushed. The red blush color is predominantly washed in pattern, although a moderate amount of dappled red striping is frequently present.

*Blush color.*—Ranges from a medium red-orange (3-D-11 Satsuma Orange) to a deep garnet red (7-L-10 Kettledrum Red) with numerous shades in between.

*Ground color.*—Ranges from 0 percent to 20 percent of the fruit surface and is an amber-yellow (10-K-4 Narcissus Yellow).

Flesh:

*Flesh color.*—Uniform yellow-gold (10-K-5) from just under the skin inward to the stone cavity. A medium number of light colored fibers are present throughout the flesh. A small amount of red flecking is present and is more noticeable as the fruit attains a higher maturity.

*Surface of pit cavity.*—The stone cavity is dark red (6-L-10 Cuba Red) with rays of red coloration extending into the flesh 9 mm (0.3543 inches) to 13 mm (0.5118 inches) from the cavity.

*Juice production.*—Juicy with afterripening.

*Flavor.*—Very pleasant and well balanced with low acidity.

*Aroma.*—Moderate in quantity and pleasant in character.

*Flesh texture.*—Firm, crisp and fine textured at commercial maturity.

*Ripening.*—Evenly throughout.

*Eating quality.*—Very good.

Stone:

*Attachment.*—Freestone with slight fiber attachments at the base of the stone. Relatively little air space is present within the cavity.

*Fibers.*—Numbers — A few tender fibers remain attached to the stone at the base. Length — Short.

*Size.*—Generally — Medium. Length — Ranges from 30 mm (1.181 inches) to 33 mm (1.299 inches). Width — 23 mm (0.9055 inches) to 26 mm (1.024 inches). Thickness — 16 mm (0.6299 inches) to 18 mm (0.7087 inches).

*Form.*—Generally — Variable from oval to slightly obovate at times.

*Apex.*—Shape — Acute, tipped with a short, acute, dentate tip.

*Color.*—Dry — Medium brown (14-D-11). A moderate amount of purplish staining is present on the stone surface, more apparent basally.

*Base.*—Shape — Slightly truncate. The base angle is clearly oblique to the stone axis.

*Sides.*—Generally — Usually unequal, but at times only slightly unequal.

*Surface.*—Rough laterally, with numerous grooves and pits. The surface is most deeply grooved laterally over the apical shoulders.

*Ventral edge.*—Moderately wide. Width — 4.0 mm (0.1575 inches) to 4.5 mm (0.1772 inches).

*Wings.*—Several low wings are present, coalesced at mid-stone and above, converging apically. Wings are at times more prominent basally.

*Dorsal edge.*—Grooved from base to apex. More narrow over the apical shoulder, deeper and wider from mid-suture to the base. The mid to basal portion of the suture is subtended by two high ridges which are occasionally cut by cross-grooves. The apical shoulder of the dorsal edge is moderately eroded and convex in form.

*Hilum.*—Distinctly outlined by a raised and grooved collar. Size — Medium. Thickness — 1.0 mm (0.0394 inches) to 1.5 mm (0.0591 inches). Form — Oval.

*Tendency to split.*—No tendency to split has been observed.

Use: Fresh market.

Although the new variety of peach tree possesses the described characteristics noted above as a result of the growing conditions prevailing in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described which produces fruit mature for commercial harvesting and shipment approximately Aug. 1 to Aug. 10 in the San Joaquin Valley of central California and somewhat remotely similar in the shape and coloration to the fruit of the "O'-Henry" peach tree (U.S. Plant Pat. No. 2,964), but distinguished therefrom in numerous respects including a more globose shape with lower acidity providing a mild, pleasant flavor.

* * * * *

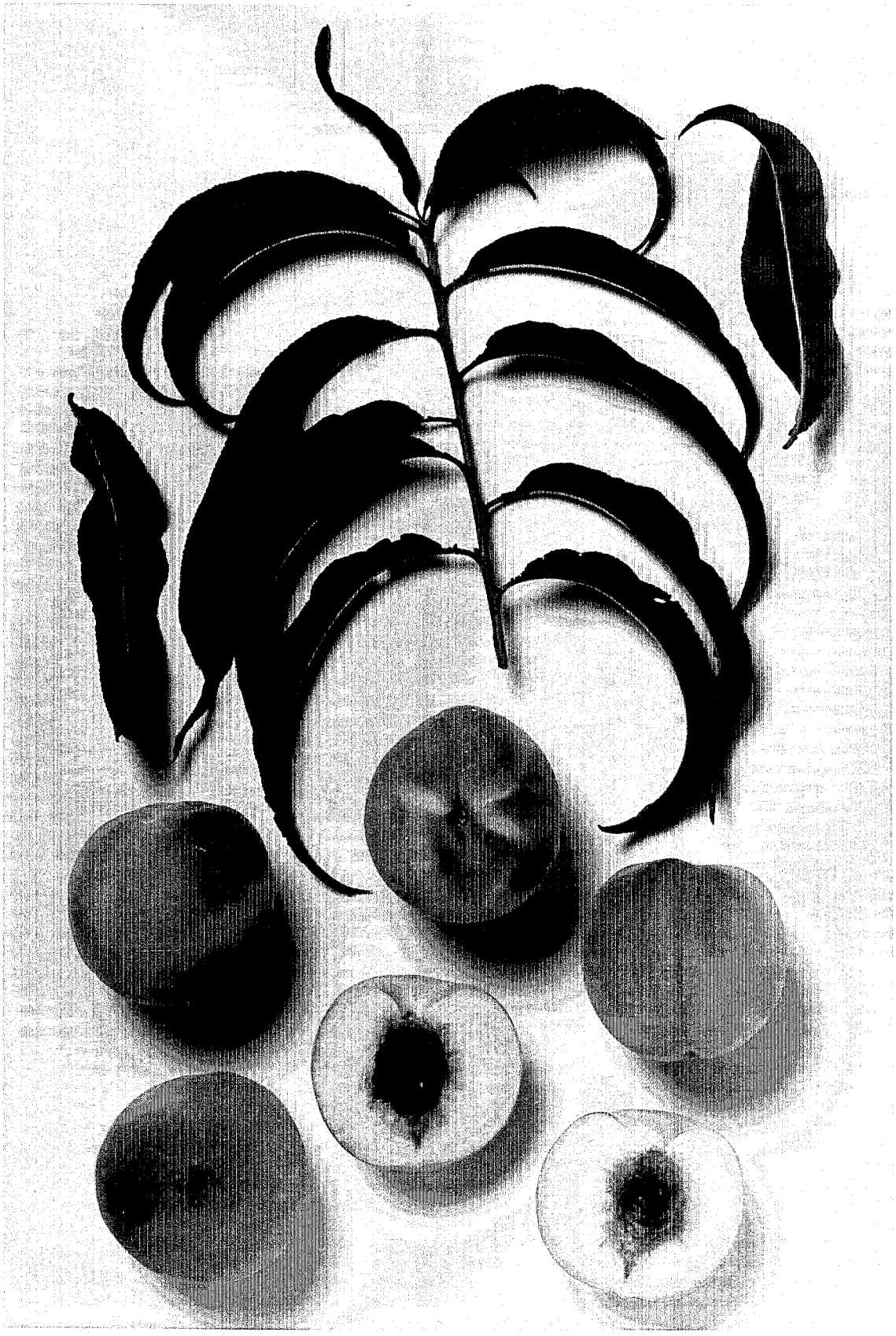

UNITED STATES PATENT AND TRADEMARK OFFICE

CERTIFICATE OF CORRECTION

PATENT NO. : PP09102

DATED : APRIL 11, 1995

INVENTOR(S) : FERNANDO C. AVILA

It is certified that error appears in the above-identified patent and that said Letters Patent is hereby corrected as shown below:

Column 1, line 26, delete "diegestive" and substitute ---digestive---.

Column 1, line 30, delete "possess" and substitute ---possessing---.

Column 1, line 36, delete "invention" and substitute ---variety---.

Column 3, line 36, delete "measurement" and substitute ---measurements---.

Column 4, line 29, delete "Mar. 7" and substitute ---Mar. 5---.

Column 4, line 36, delete "expended" and substitute ---expanded---.

Signed and Sealed this

Twenty-ninth Day of August, 1995

*Attest:*

Bruce Lehman

BRUCE LEHMAN

*Attesting Officer*

*Commissioner of Patents and Trademarks*